United States Patent [19]

Elff et al.

[11] Patent Number: 4,872,193
[45] Date of Patent: Oct. 3, 1989

[54] LITHOTRIPSY WORKSTATION

[75] Inventors: Manfred Elff, Hamburg; Wilfried G. Pfeiffer, Quickborn; Horst-Hartwig Schwieker, Hamburg; Dieter H. C. Christiansen, Schönberg, all of Fed. Rep. of Germany

[73] Assignee: U.S. Philips Corporation, New York, N.Y.

[21] Appl. No.: 173,699

[22] Filed: Mar. 25, 1988

[30] Foreign Application Priority Data

Apr. 4, 1987 [DE] Fed. Rep. of Germany ....... 3711404
Jul. 18, 1987 [DE] Fed. Rep. of Germany ....... 3723920

[51] Int. Cl.⁴ ............................................. A61B 17/22
[52] U.S. Cl. ..................... 378/196; 128/328; 378/208
[58] Field of Search ............... 378/196, 53, 51, 208, 378/205; 128/328, 29 A

[56] References Cited

U.S. PATENT DOCUMENTS 4,705,026 11/1987 Chaussy et al. ............. 128/328
4,741,008 4/1988 Franke ........................ 378/53
4,764,944 8/1988 Finlayson .................... 378/205
4,796,613 1/1989 Heumann et al. ............. 378/196
4,811,725 3/1989 Grasser ....................... 128/24 A

FOREIGN PATENT DOCUMENTS 0257429 3/1988 European Pat. Off. ............ 128/328
8528785 8/1986 Fed. Rep. of Germany .

OTHER PUBLICATIONS

Thomas Curry, M. D. et al., "Shock Wave Lithotripsy: Its Impact on Radiologists" Diagnostic Imaging, Mar. 1987, pp. 96–101.

Primary Examiner—Carolyn E. Fields
Assistant Examiner—Joseph A. Hynds
Attorney, Agent, or Firm—Thomas A. Briody; Jack E. Haken; Jack D. Slobod

[57] ABSTRACT

A lithotripsy workstation which can also be used for X-ray examination includes an X-ray device (5, 6) which is pivotable about a horizontal axis (7), and a shock wave generator (18) which is pivotable about an inclined axis (17) which intersects the horizontal axis. The focal point of the shock wave generator (18) coincides with this point of intersection, even when the shock wave generator is pivoted to the left or to the right to a position which is suitable for crushing a calculus in the left-hand kidney or the right-hand kidney.

6 Claims, 4 Drawing Sheets

LITHOTRIPSY WORKSTATION

The invention relates to a lithotripsy workstation, comprising a patient table underneath of which there is arranged a shock wave generator, and also comprising an X-ray device for localizing concrements, which comprises an X-ray source and an image converter which is centred with respect thereto.

From DE-GM 85 28 785 a lithotripsy workstation is known which comprises a patient table, an X-ray device which consists of two X-ray sources and two image converters for localizing renal calculi, and two shock wave generators which are displaceable in the direction of their focal point and which are arranged underneath the top of the patient table. Each of the shock wave generators is associated with a respective kidney.

It is an object of the present invention to construct a lithotripsy workstation of the kind set forth which requires fewer means.

SUMMARY OF THE INVENTION

This object is achieved in accordance with the invention in that (a) the X-ray device is pivotable about a first axis which extends perpendicularly with respect to the longitudinal direction of the table top and horizontally and perpendicularly to the central ray or axis of the X-ray device, which first axis intersects said central ray in a point which is referred to as the point of intersection, (b) the shock wave generator is connected to a pivot arm which is pivotable about a second, inclined axis which extends through the focal point of the shock wave generator and which is positionable to define a perpendicular plane in conjunction with the longitudinal direction of the table, (c) the pivot arm, when so positioned, and the shock wave generator are arranged with respect to the X-ray device so that the point of intersection coincides with the focal point.

Because the X-ray device is pivotable about the first axis, the patient can be irradiated from two different directions, enabling the localization of a renal calculus and its positioning in the centre of the shock wave generator by means of only one x-ray source and only one image converter. When the renal calculus has been positioned at the point of intersection, the shock wave generator can be pivoted to the optimum position for the crushing of the calculus, pivoting being possible to the left-hand side as well as to the right-hand side of the patient, so that renal calculi in the left-hand kidney as well as in the right-hand kidney can be crushed by means of only one shock wave generator.

In a further embodiment in accordance with the invention, a bearing for the pivot arm is pivotable about a third axis which extends underneath the pivot arm and preferably horizontally so as to be parallel to plane of the table top, in particular, its longitudinal direction . This embodiment enables, by pivoting about the second and the third axis, the shock wave generator to be pivoted to a parking position in which it does not interfere with the X-ray examination by means of the x-ray device. However, it can also be pivoted to a service position in which the shock wave generator is particularly simply accessible for service purposes.

In a further embodiment in accordance with the invention, the image converter and/or the X-ray source are connected to an arm which is perpendicular ot the first axis in order to be pivotable about the longitudinal axis of said arm. This enables reversal of the beam path by first pivoting the part which is pivotably connected to the arm through approximately 90° with respect to the examination position, after which the x-ray device is pivoted through 180° about the first axis, and finally said part is pivoted back to the examination position again.

A further embodiment in accordance with the invention by means of which X-ray examinations can be performed also in the case of inclined incidence of the beam in a plane perpendicular to the longitudinal direction of the table is characterized in that the patient table is pivotable, independently of the X-ray device, about a vertical axis extending through the point of intersection.

the pivoting of the patient table about the vertical axis enables X-ray images to be formed with a substantially arbitrary direction of incidence of the beam in relation to the patient.

In a further embodiment in accordance with the invention, the pivot arm for the shock wave generator is connected to the patient table. This enables lithotripsy to be performed in any arbitrary pivotal position of the patient table, i.e. without pivoting the table back to its initial position.

BRIEF DESCRIPTION OF THE DRAWINGS

The invention will be described in detail hereinafter with reference to the drawings. Therein.

DETAILED DESCRIPTION OF THE PREFERRED EMBODIMENT

Figure 1:
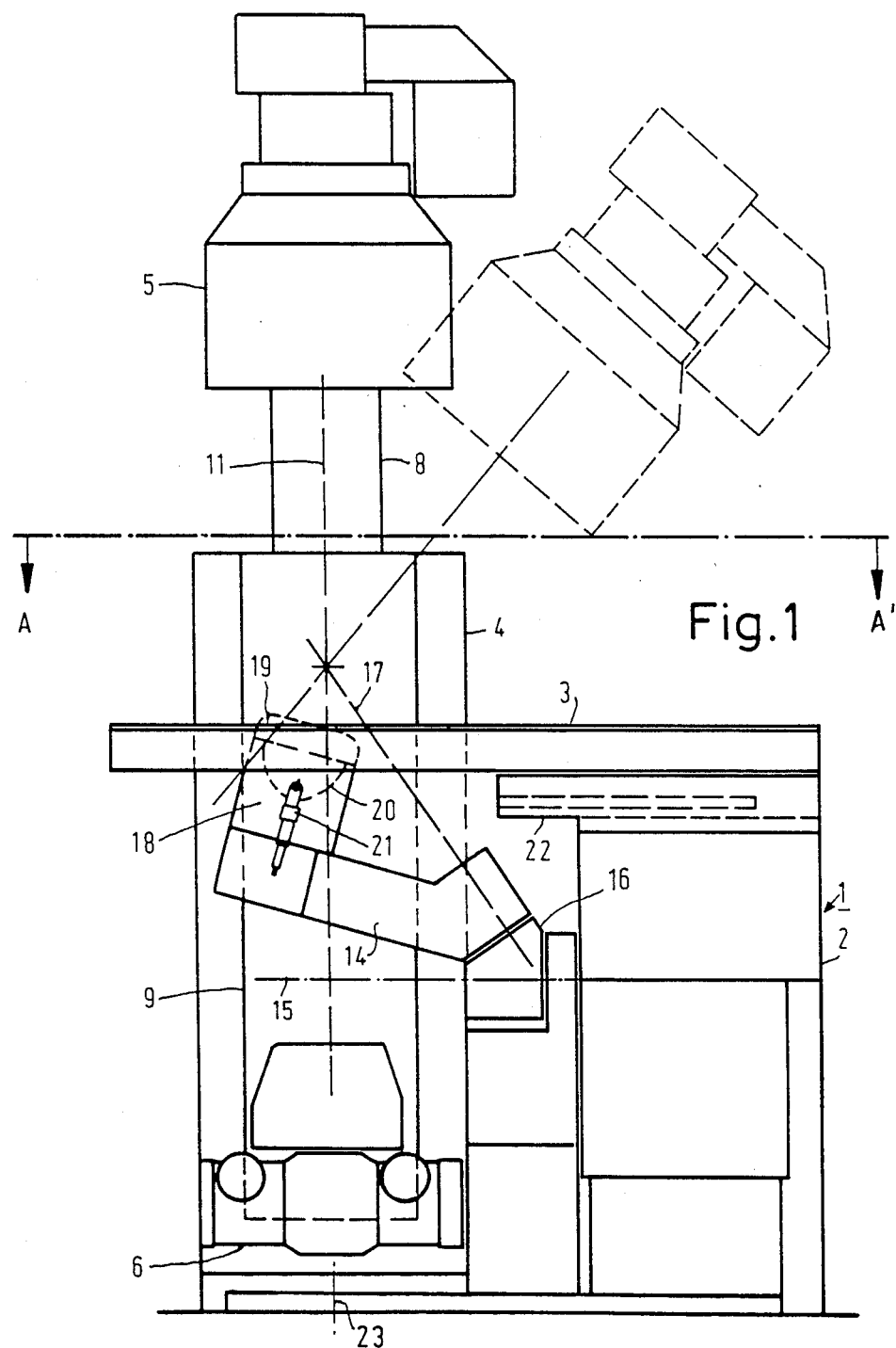
FIG. 1 is a side elevation of a workstation in accordance with the invention.
Figure 2:
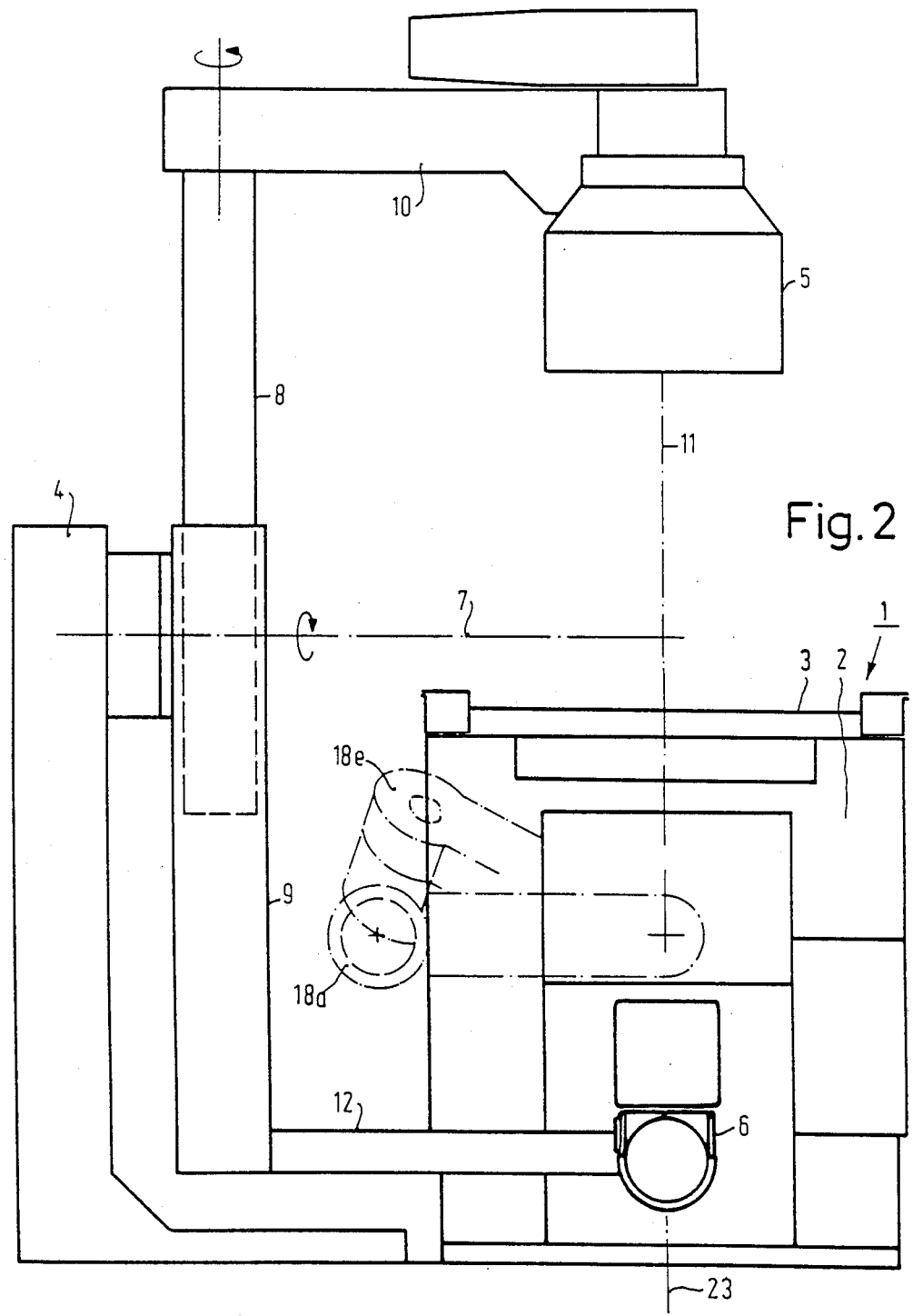
FIG. 2 is a front view of such a workstation, be it with a different position of the shock wave generator.

The reference numeral 1 in the FIGS. 1 and 2 denotes a patient table comparing a base 2 and a generally planar horizontal top 3 which is movable in its longitudinal direction (horizontally in FIG. 1), its transverse direction (perpendicularly to the plane of drawing in FIG. 1) and in its vertical direction. An X-ray device is mounted on a stand 4 so as to be pivotable about a horizontal axis 7 which extends parallel to the plane of table
top 3 and, more specifically
perpendicularly to the longitudinal direction of the table top 3. The X-ray device comprises an X-ray source 6 which is secured to a carrier 12 at the end of a hollow arm 9 having a center axis 11, which is pivotable about the axis 7, and also comprises an X-ray image intensifier 5. The X-ray image intensifier 5 is secured to a carrier 10 which itself is connected to an end of an arm 8 so as to be pivotable about the longitudinal axis 11 thereof. The arm 8 can be shifted inside the hollow arm 9 so that the distance between the X-ray image intensifier 5 and the X-ray source 6 along axis 11 can be varied.

Underneath the table top 3 there is arranged a bearing holder 16 which is pivotable about a horizontal axis 15, extending parallel to the longitudinal direction of the table, and in which a pivot arm 14 is journalled so as to be pivotable about an axis 17 which encloses an angle of approximatly 55° with respect to the axis 15. A shock wave generator 18 is secured to the free end of the pivot arm 14. The shock wave generator comprises a cavity which is filled with water and which is sealed by a membrane 19, said cavity being shaped as an ellipsoid 20 in one focus of which there is arranged a spark gap 21 for generating a shock wave. The other focus of the ellipsoid, referred to hereinafter as the focal point, is situated on the pivot axis 17. The energy generated by the shock wave is concentrated therein in known manner. The energy for the crushing of the calculi can alternatively be generated in a different manner, for example, by arranging ultrasound transducers on a suitably shaped body of rotation, the energy of said transducers being focussed in one point.

When the bearing holder is situated in the position (see FIGS. 1 and 3) in which the pivot axis 17 and the pivot axis 15 define a vertical plane parallel to the longitudinal direction of the table top 3, the focal point coincides with the point of intersection of the central ray with the horizontal pivot axis 7. When the patient has been positioned in advance so that the calculus to be crushed is situated in this point of intersection, the pivot arm 14 can be pivoted about the axis 17 in this position of the bearing holder until considering the anatomy of the patient, an optimum position is obtained, without the focussing being influenced thereby. The described workstation can be used not only for lithotripsy but also for urological or other X-ray examinations, as will be explained hereinafter.

In order to make undertable radiographs, the shock wave generator 18 is pivoted out of the beam path. This can be realized, for example, by pivoting the bearing holder 16 about the axis 15 so that the axes 15 and 17 define a horizontal plane and by pivoting the pivot arm through 180° about the axis 17. It then occupies the parking position which is denoted by broken lines and the reference numberal 18a in FIG. 2.

However, it is also possible to perform X-ray examinations with a reversed beam path. To this end, first the arm 8 is completely moved into the hollow arm 9, the carrier 10 is pivoted about the arm 8, and subsequently the X-ray device is pivoted through 180° about the axis 7, the X-ray source then moving upwards around the foot end whilst the image intensifier moves downwards in the space between the table 1 and the stand 4. The carrier 10 is then pivoted back again, so that the X-ray source 6 and the image intensifier 5 are aligned once more. In this position of the X-ray tube Bucky exposures can also be made by means of a cassette holder 22 which is arranged underneath the table top 3 and which is displaceable in the longitudinal direction of the table.

For the localization of concrements in the human body, preferably renal calculi, the patient is first irradiated in the position of the X-ray device which is denoted by non-interrupted lines in FIG. 1, after which the X-ray device is pivoted about the axis 7 (denoted by a broken line for the image intensifier 5 in FIG. 1) and the patient is irradiated again from the perspective thus changed. This enables determination of the position in space of the calculus to be crushed and to shift the table top so that the calculus is situated at the point of intersection of the horizontal axis 7 and the central ray 11.

Subsequently, the bearing holder 16 is pivoted so that the pivot axes 15 and 17 again define a vertical plane. In this position of the bearing holder 16, the shock wave generator 18 is always focussed on the point of intersection of the pivot axis 7 and the central ray 11, regardless of the position of the pivot arm 14, and remains focussed thereon also when the pivot arm is pivoted to the optimum position for crushing the calculus.

Figure 3:
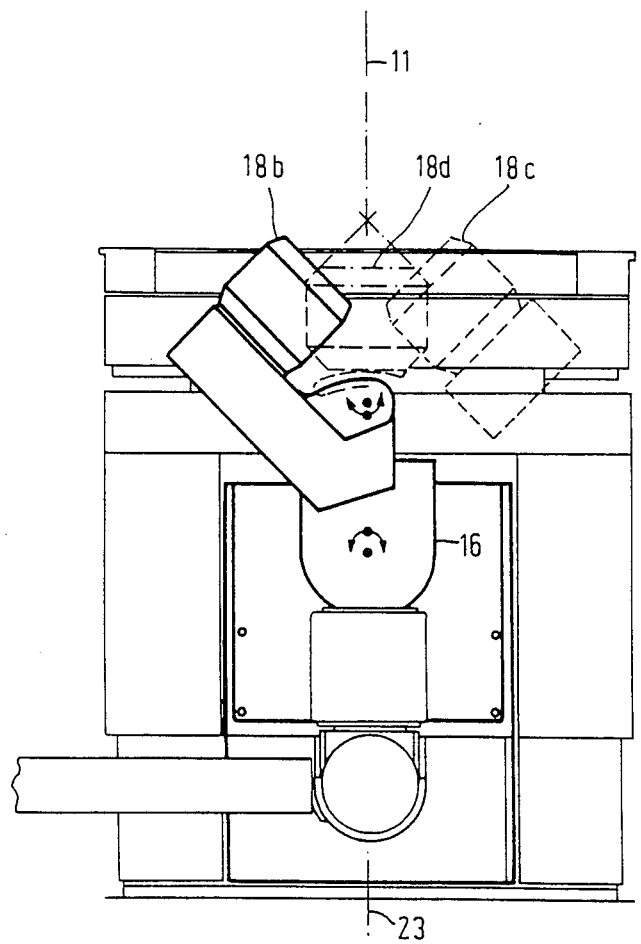
FIG. 3 shows a detail of the view shown in FIG. 2, with different positions of the shock wave generator.

When a calculus in the right-hand kidney is crushed, the shock wave generator is pivoted to the left, as denoted by noninterrupted lines and the reference numeral 18b in FIG. 3, until the line of application of the shock wave generator defines, in conjunction with the horizontal pivot axis, at least substantially a vertical plane which extends perpendicularly to the longitudinal direction of the table. The direction of application then extends at an angle of approximately 43° with respect to the horizontal. When a calculus in the left-hand kidney is crushed, the shock wave generator is pivoted to the right in an analogous manner (position 18c denoted by broken lines) and when a biliary calculus is concerned, it is moved to a central position (18d or FIG. 1).

In all these cases the membrane 19 of the shock wave generator 18 must be in direct contact with the body of the patient, consequently, the table top 3 must be provided with a suitably shaped opening (not shown).

In the case of a shock wave generator in which the shock wave is generated by means of a spark gap, electrodes must be exchanged at regular intervals. To this end, the pivot arm 14 is pivoted out of the position shown in the FIGS. 1, 3 (position 18d) through 90° about the axis 17 and the bearing holder 16 is pivoted through 90° about the axis 15, so that the shock wave generator occupies the position which is denoted by the reference numeral 18e in FIG. 2 and in which the opening of the ellipsoid 20 in the shock wave generator is directed downwards. In this position the spark gap electrode 21 can be removed, without the water filling in the space formed by the ellipsoid 20 and the membrane 19 being lost.

The apparatus described thus far only enables the patient arranged on the patient table 1 to be irradiated in such an irradiation direction that the central ray always remains in a vertical plane containing the longitudinal axis of the table. The operator can approach the patient from one side only (from the right in FIG. 2). In many cases, however, it is desirable that the patient is arranged so as to be accessible from both sides, or that the patient can be irradiated from other directions.

To this end, the patient table, together with the shock wave generator 18 connected thereto via the parts 16, 14, is pivotable about a vertical axis 23 which extends through the focal point and hence coincides with the central ray 11 in the position of the X-ray device 5, 6 shown in the FIGS. 1 and 2. To this end, the frame of the base 2 of the patient table 1 which is only diagrammatically shown in the drawings can be journalled in a central bearing or ring mount (not shown) in the floor. Moreover, on the base there may be provided rollers (not shown) which are situated at a distance from the axis 23, which rollers take up part of the weight of the table 1 and roll on the floor or on a rail installed therein.

Figure 4:
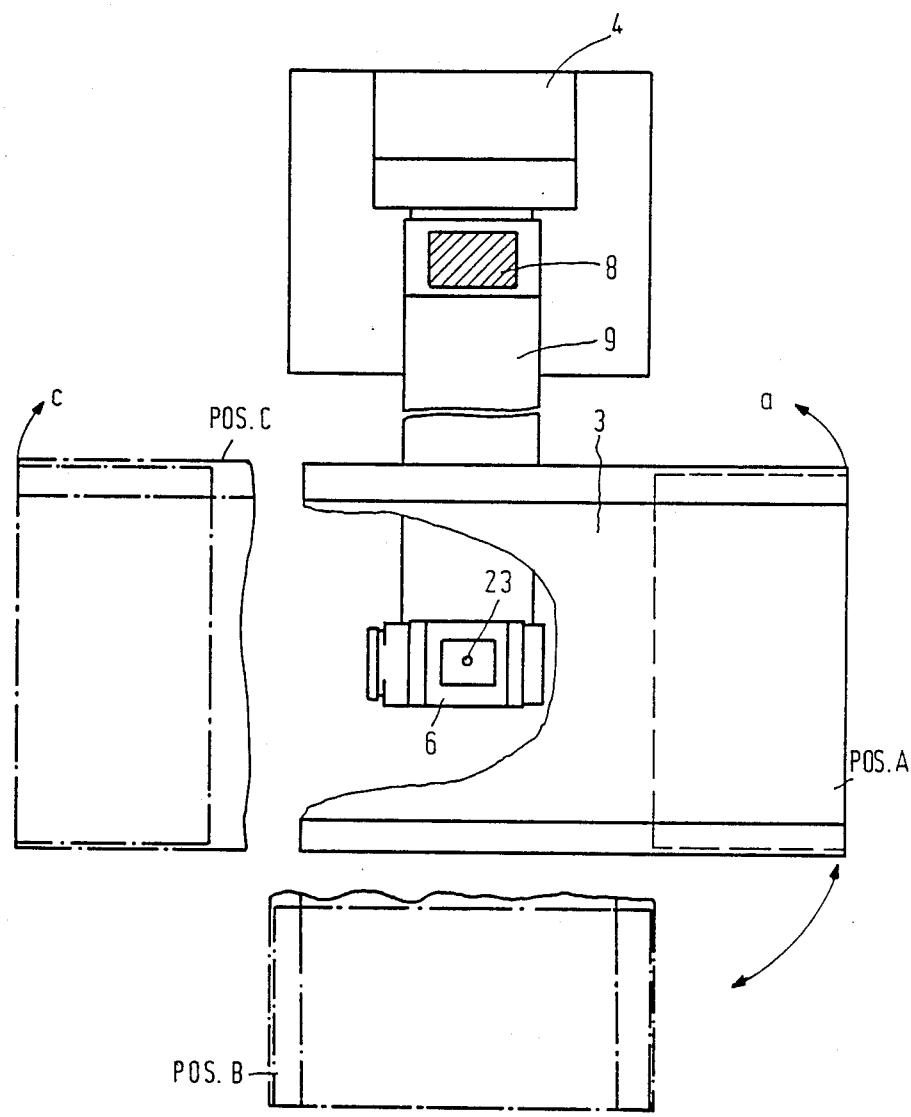
FIG. 4 is a plan view of such a workstation.

FIG. 4 is a plan view of the apparatus taken along the line A, A' in FIG. 1 (the table top 3 is shown partly in a broken-away view and the shock wave generator has been omitted, together with the parts 14 and 16) and illustrates the examination positions then possible. The position A is the position shown in FIG. 1.

The position B is reached by pivoting the patient table through 90° about the horizontal axis 23. This position is attractive in that the patient is then accessible from both sides. In this position they are formed by the arms 8, 9 and the carriers 10, 12 can be pivoted directly through 180° about the axis 7, so that the patient can be irradiated from arbitrary directions by means of a central ray 11 which is situated in a plane perpendicular to the longitudinal axis of the table.

The patient table 10 can also be displaced to the position C in which the other side of the patient (in comparison with the position A) is accessible for the operator. In all positions the table top 3 can also be displaced beyond the head end. Moreover, in the positions A and C the patient table can also be pivoted counterclockwise and clockwise through 45°, as denoted by the arrows a and c, resulting in a total pivot range of 270°.

What is claimed is:

1. A lithotripsy workstation, comprising a generally horizontal patient table top (3) with respect to which are arranged a shock wave generator (18), and an X-ray device for localizing of concrements, which X-ray device comprises an X-ray source (6) and an image converter (5) which are spaced apart along an X-ray axis (11) passing through the table top (3), characterized in that a) the X-ray device (5, 6) is pivotable about a generally horizontal first axis (7) which extends perpendicularly to the X-ray axis (11) of the X-ray device, which first axis (7) intersects said X-ray axis (11) in a point, above the table top, which is referred to as the point of intersection,
    (b) the shock wave generator (18) is carried by a pivot arm (14) which is pivotable about a second, inclined axis (17), said shock wave generator (18) having a focal point through which said inclined axis (17) extends,
    (c) said means for maintaining said inclined axis (17) oriented
    with respect to the X-ray device (5, 6) so that the point of intersection coincides with the focal point.

2. A device as claimed in claim 1, characterized in that the image converter and X-ray source are carried by an arm means (8,9) defining the X-ray axis (11), and means (4) supporting said arm means for pivoting said arm means (8,9) about said first axis (7)

3. A device as claimed in claim 2, characterized in that said arm means (8,9) comprises a first arm (8) axis 11 in a hollow arm (9), said hollow arm (9) being coupled to said means supporting said arm means (8,9).

4. A device as claimed in claim 1, characterized in that the patient table top (3) is pivotable, independently of the X-ray device (4, 5, 6), about a vertical axis (23) extending through the point of intersection.

5. A device as claimed in claim 1, wherein said patient table top has a base (2) and said means for maintaining the orientation of said inclined axis (17) comprises means (16) underneath the patient table top coupling said pivot arm (14) to said base (2).

6. A device as claimed in claim 5 further comprising means for pivoting said base (2), independently of said X-ray device (4, 5, 6) about a vertical axis (23) extending through said point of intersection.

* * * * *